United States Patent
Shibata et al.

(10) Patent No.: US 9,282,937 B2
(45) Date of Patent: Mar. 15, 2016

(54) COUCH WITH PATIENT-INCLINING DEVICE

(71) Applicant: MITSUBISHI HEAVY INDUSTRIES, LTD., Tokyo (JP)

(72) Inventors: Hiroyuki Shibata, Tokyo (JP); Tetsuya Goto, Tokyo (JP); Masayuki Matsuda, Tokyo (JP); Yoshio Sugimoto, Hiroshima (JP)

(73) Assignee: MITSUBISHI HEAVY INDUSTRIES, LTD., Tokyo (JP)

( * ) Notice: Subject to any disclaimer, the term of this patent is extended or adjusted under 35 U.S.C. 154(b) by 11 days.

(21) Appl. No.: 14/379,337

(22) PCT Filed: Dec. 21, 2012

(86) PCT No.: PCT/JP2012/083341
§ 371 (c)(1),
(2) Date: Aug. 18, 2014

(87) PCT Pub. No.: WO2013/125146
PCT Pub. Date: Aug. 29, 2013

(65) Prior Publication Data
US 2015/0020313 A1    Jan. 22, 2015

(30) Foreign Application Priority Data
Feb. 20, 2012  (JP) ................................. 2012-034235

(51) Int. Cl.
*A61B 6/04* (2006.01)
*A61G 7/005* (2006.01)
(Continued)

(52) U.S. Cl.
CPC .............. *A61B 6/0407* (2013.01); *A61G 7/005* (2013.01); *A61G 7/018* (2013.01); *A61B 6/03* (2013.01); *A61B 6/0457* (2013.01); *A61N 5/1049* (2013.01); *A61N 5/1069* (2013.01)

(58) Field of Classification Search
CPC ...... A61B 6/0407; A61B 6/0457; A61B 6/03; A61G 7/005; A61G 7/018; A61G 13/04; A61G 2210/50; A61N 5/1069; A61N 5/1049
See application file for complete search history.

(56) References Cited

U.S. PATENT DOCUMENTS

| | | | | |
|---|---|---|---|---|
| 4,131,801 A | * | 12/1978 | Hogan | A61B 6/0457 108/6 |
| 4,912,754 A | * | 3/1990 | Van Steenburg | A61B 6/0457 378/179 |

(Continued)

FOREIGN PATENT DOCUMENTS

| | | |
|---|---|---|
| CN | 101211676 | 7/2008 |
| EP | 1738798 | 1/2007 |

(Continued)

OTHER PUBLICATIONS

International Search Report issued Feb. 19, 2013 in corresponding International Application No. PCT/JP2012/083341.

(Continued)

*Primary Examiner* — David E Sosnowski
*Assistant Examiner* — Eric Kurilla
(74) *Attorney, Agent, or Firm* — Wenderoth, Lind & Ponack, L.L.P.

(57) ABSTRACT

A couch with a patient-inclining device (10) includes a tabletop (28), a pair of second rails (15) arranged below the tabletop, a second moving section (16) having a pair of second sliders (17) which are movable on the pair of second rails, a pair of block bodies (22A and 22B) which are movable on the pair of second rails, drive mechanisms (23A and 23B) which linearly move the block bodies with respect to the second moving section, a support section (26) provided on the second moving section to support the tabletop, and levers (27A and 27B), each having one end connected to the tabletop and the other end connected to the associated one of the pair of block bodies.

4 Claims, 6 Drawing Sheets

(51) Int. Cl.
*A61G 7/018* (2006.01)
*A61N 5/10* (2006.01)
*A61B 6/03* (2006.01)

(56) References Cited

U.S. PATENT DOCUMENTS

| | | | | |
|---|---|---|---|---|
| 5,013,018 | A * | 5/1991 | Sicek | A61B 6/0457 378/209 |
| 5,299,334 | A * | 4/1994 | Gonzalez | A61G 7/005 5/607 |
| 6,282,736 | B1 * | 9/2001 | Hand | A61B 6/0428 5/600 |
| 6,637,056 | B1 * | 10/2003 | Tybinkowski | A61B 6/0457 378/209 |
| 6,640,363 | B1 * | 11/2003 | Pattee | A61G 13/04 5/601 |
| 7,373,676 | B2 | 5/2008 | Markovic et al. | |
| 7,818,838 | B2 | 10/2010 | Erbel et al. | |
| 8,242,465 | B2 * | 8/2012 | Iwata | G01N 23/00 250/491.1 |
| 2003/0145383 | A1 * | 8/2003 | Schwaegerle | A61G 13/04 5/610 |
| 2004/0172758 | A1 * | 9/2004 | Alakkat | A61B 6/04 5/610 |
| 2006/0248648 | A1 * | 11/2006 | Kratzmaier | A61G 13/02 5/600 |
| 2008/0028526 | A1 * | 2/2008 | Kato | A61B 5/0555 5/601 |
| 2008/0086816 | A1 * | 4/2008 | Farooqui | A61B 6/0457 5/601 |
| 2009/0126116 | A1 * | 5/2009 | Lamb | A61G 13/08 5/619 |
| 2009/0156930 | A1 | 6/2009 | Ein-Gal | |
| 2010/0020939 | A1 * | 1/2010 | Yoshida | A61B 6/04 378/197 |
| 2012/0023671 | A1 * | 2/2012 | Miyano | A61B 6/0407 5/601 |
| 2012/0324648 | A1 * | 12/2012 | Amano | A61B 6/037 5/601 |
| 2013/0276233 | A1 * | 10/2013 | Bergfjord | A61G 13/06 5/611 |
| 2014/0033433 | A1 * | 2/2014 | Kimishima | A61B 6/0407 5/601 |

FOREIGN PATENT DOCUMENTS

| | | |
|---|---|---|
| GB | 723572 | 2/1955 |
| JP | 2006-051215 | 2/2006 |
| JP | 3132936 | 6/2007 |
| JP | 2011-182868 | 9/2011 |
| WO | 01/72226 | 10/2001 |
| WO | 2010/049660 | 5/2010 |

OTHER PUBLICATIONS

Translation of Written Opinion of the International Searching Authority issued Feb. 19, 2013 in corresponding International Application No. PCT/JP2012/083341.
BrainLAB ExacTrac IGRT Solution Brochure, 2005.
Extended European Search Report issued Aug. 28, 2015 in European Application No. 12869200.1.
Office Action issued Dec. 1, 2015 in corresponding Chinese Application No. 201280069266.0 (with English translation of Search Report).

* cited by examiner

COUCH WITH PATIENT-INCLINING DEVICE

TECHNICAL FIELD

The present invention relates to a couch with a patient-inclining device.

Priority is claimed on Japanese Patent Application No. 2012-034235, filed Feb. 20, 2012, the content of which is incorporated herein by reference.

BACKGROUND ART

Conventionally, a radiation irradiation device for performing radiation treatment is provided with a couch having a bed moving relative to an isocenter of the radiation irradiation device, for the purpose of determining an irradiation position of radiation onto a patient.

Such a couch is provided with a device tilting a patient placed on the bed for the purpose of maintaining the patient in various postures. For example, Patent Literature 1 discloses a treatment table for a radiation treatment device. The treatment table for a radiation treatment device disclosed in Patent Literature 1 may horizontally move a patient along three axes orthogonal to each other.

In addition, Patent Literature 2 discloses a device capable of rotatably moving the patient around the three respective axes, in addition to the horizontal movement of the patient along the three axes.

CITATION LIST

Patent Literature

[Patent Literature 1]
Japanese Unexamined Patent Application, First Publication No. 2006-51215
[Patent Literature 2]
U.S. Pat. No. 7,373,676

DISCLOSURE OF INVENTION

Technical Problem

In order to irradiate a proper part of a patient with radiation, a position and an angle at which the patient is irradiated with radiation are preferably set to have a high degree of freedom, and it is preferable that the degree of freedom be six axes defined by combination of the horizontal movement and the rotation movement as disclosed in Patent Literature 2. However, a couch having a degree of freedom of six axes causes an increase in height and a possibility of manufacturing cost being increased by an increase in the number of parts.

The present invention has been made in view of the above problem, and an object of the present invention is to provide a compact and low-cost couch with a patient-inclining device.

Solution to Problem

According to a first aspect of the present invention, a couch with a patient-inclining device includes a tabletop on which a test object is placed, a pair of rails arranged in one direction below the tabletop, a moving section having a pair of sliders movable on the pair of rails, a pair of block bodies movable on the pair of rails, drive mechanisms linearly moving the block bodies in the one direction with respect to the moving section, a support section provided on the moving section to support the tabletop, and levers, each having one end connected to the tabletop and the other end connected to the associated one of the pair of block bodies. The drive mechanisms include a first drive mechanism moving one of the pair of block bodies with respect to the moving section and a second drive mechanism moving the other of the pair of block bodies with respect to the moving section. The levers include a first lever provided at the one of the pair of block bodies and a second lever provided at the other of the pair of block bodies. The one end of the first lever and the one end of the second lever are connected to the tabletop at positions different from each other, wherein the positions are different from the support section at the tabletop.

In addition, according to a second aspect of the present invention, in the couch with a patient-inclining device according to the first aspect, at least one of the first and second drive mechanisms may include a rod-shaped threaded section extending in parallel with one of the rails and having a thread formed on an outer surface, and a nut section provided at one of the block bodies so that the threaded section is screwed to the nut section, and the threaded section may axially rotate relative to the nut section, thereby allowing the block body to move with respect to the moving section.

In addition, according to a third aspect of the present invention, in the couch with a patient-inclining device according to the first aspect, the support section may connect the moving section to the tabletop such that the tabletop is pivotable around a predetermined center of rotation with respect to the moving section.

In addition, according to a fourth aspect of the present invention, in the couch with a patient-inclining device according to the first aspect, at least one of the one end and the other end of each of the levers may be provided with a joint having a degree of freedom of two or more axes.

Advantageous Effects of Invention

According to the above description, a compact and low-cost couch with a patient-inclining device is obtained.

DESCRIPTION OF EMBODIMENTS

Hereinafter, a couch with a patient-inclining device 10 according to an embodiment of the present invention will be described with reference to the drawings.

Figure 1:
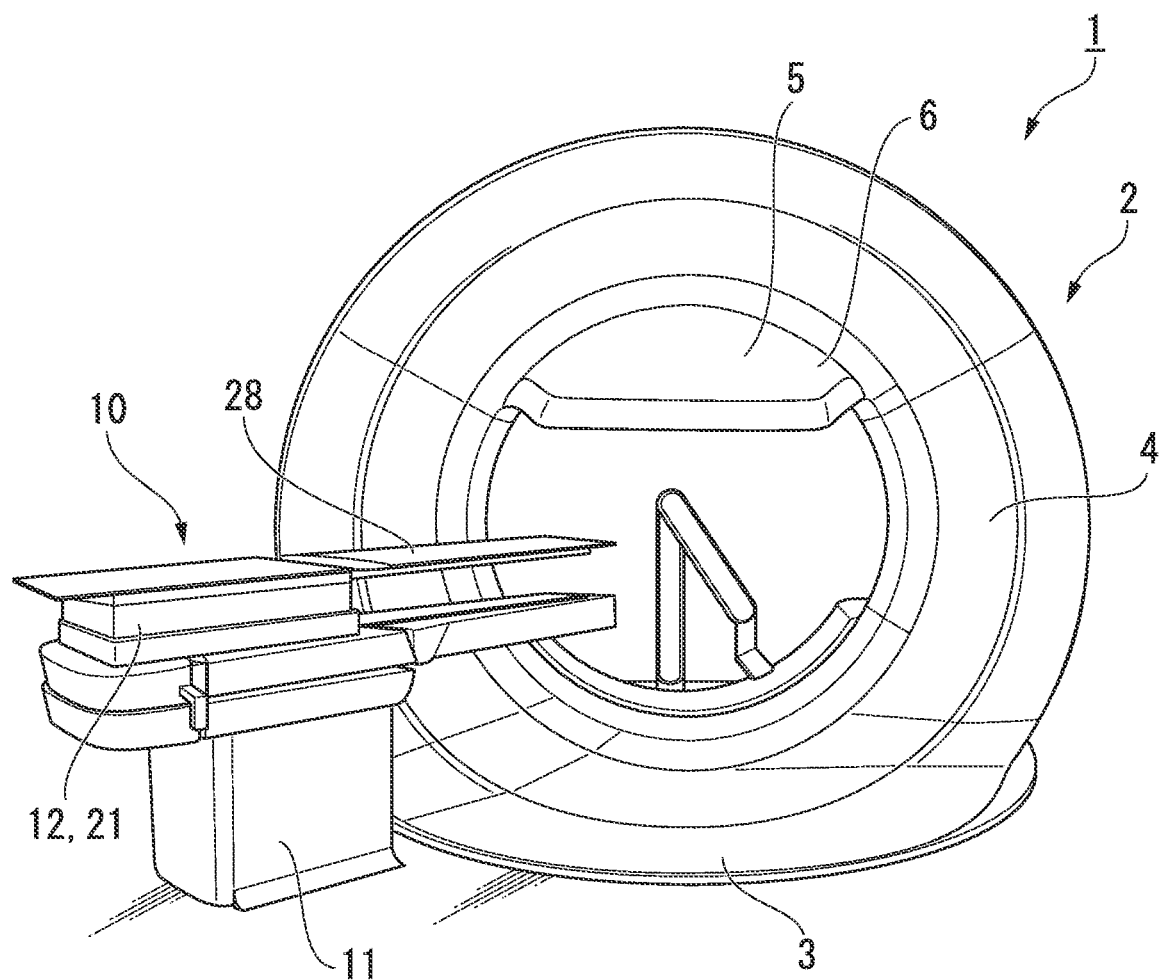
FIG. 1 is a perspective view illustrating a couch with a patient-inclining device according to an embodiment of the present invention.
Figure 2:
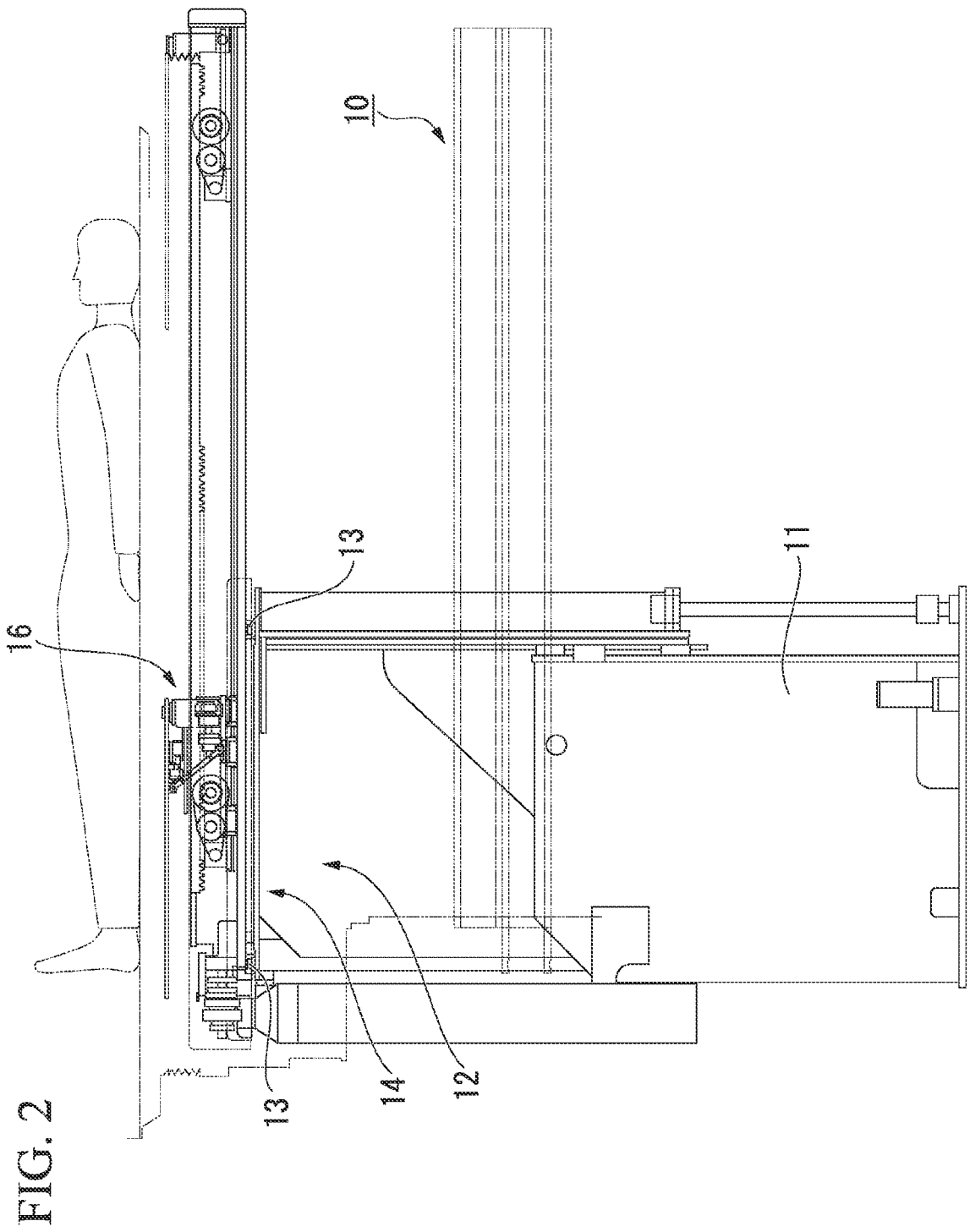
FIG. 2 is a side view illustrating a partial configuration of the couch.
Figure 3:
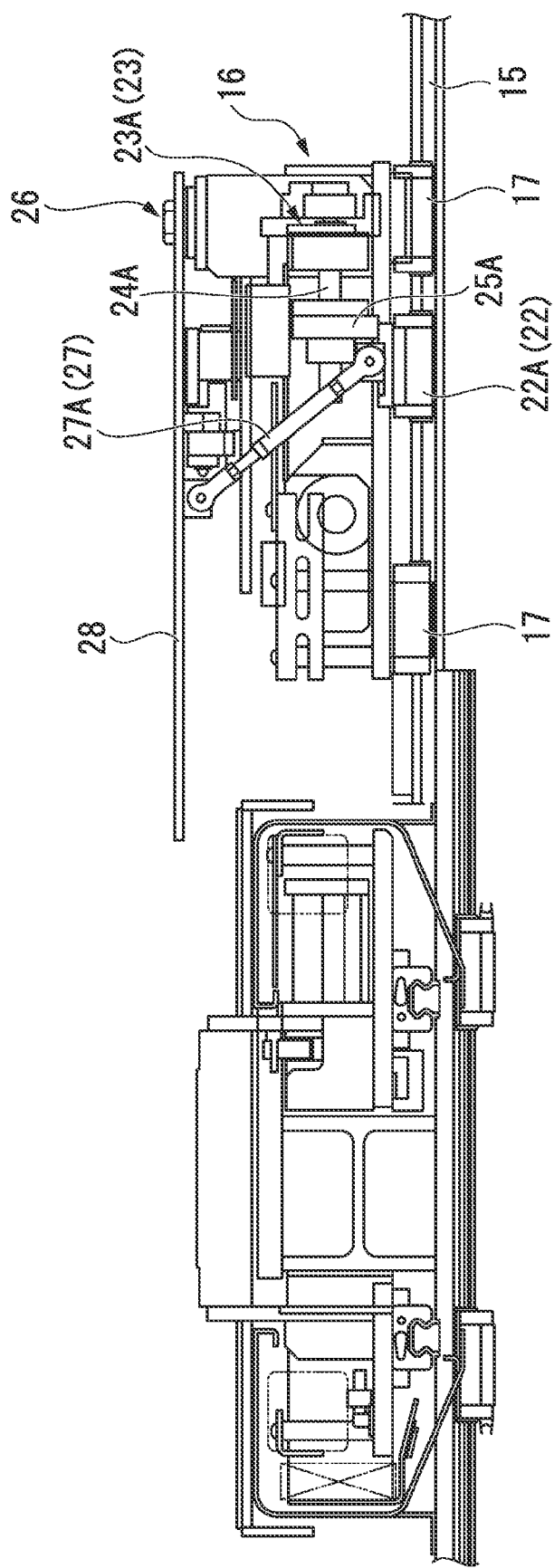
FIG. 3 is an enlarged view of a portion of FIG. 2.
Figure 4:
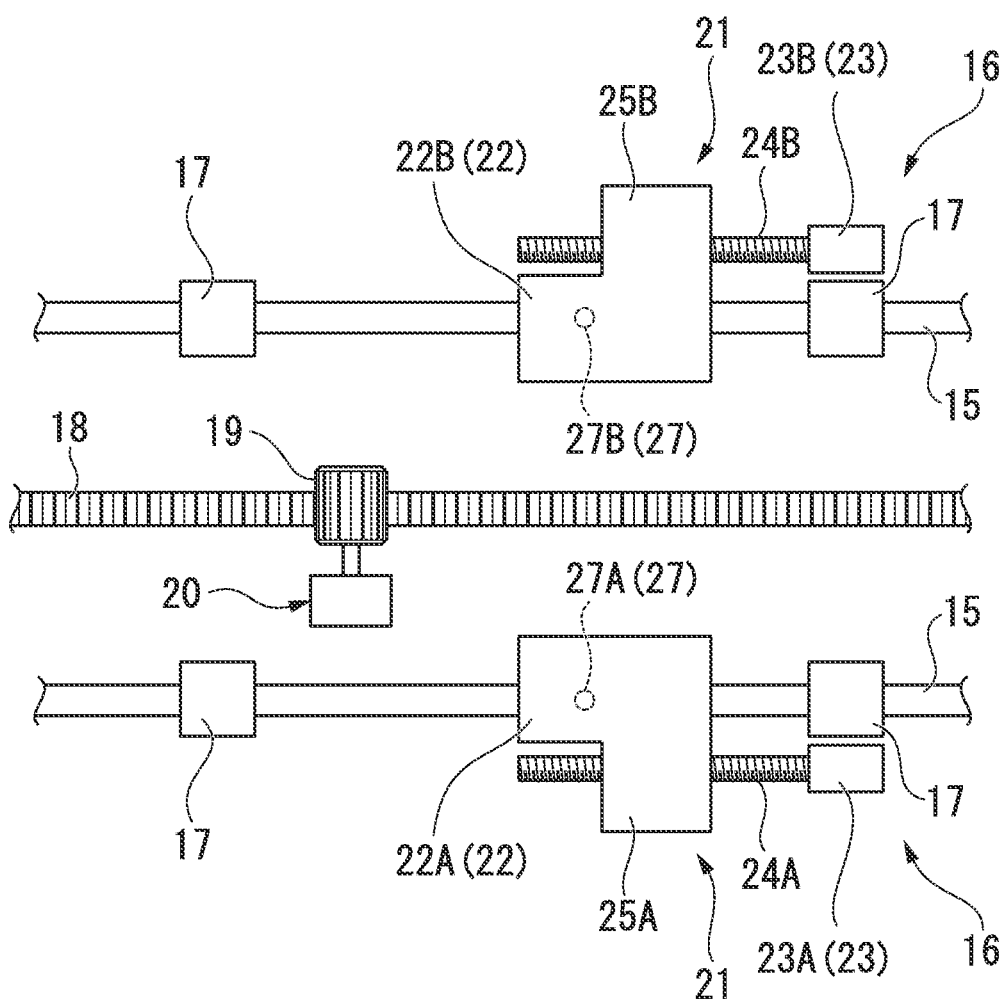
FIG. 4 is a top view schematically illustrating a portion of the couch.

FIG. 1 is a perspective view illustrating a radiation treatment system 1 including the couch with a patient-inclining device 10 according to the embodiment. FIG. 2 is a side view illustrating a partial configuration of the couch with a patient-inclining device 10. FIG. 3 is an enlarged view of a portion of FIG. 2. FIG. 4 is a top view schematically illustrating a portion of the couch with a patient-inclining device 10.

The couch with a patient-inclining device 10 (hereinafter, simply referred to as "a couch 10") of the embodiment is applied, for example, as a portion of the radiation treatment system 1 including a radiation irradiation device 2.

First, a schematic configuration of the radiation treatment system 1 will be described.

As shown in FIG. 1, the radiation treatment system 1 includes a radiation irradiation device 2 for irradiating a patient with radiation while moving around the patient, a CT device 6 for performing an X-ray CT (computerized tomography) test, and a couch 10 of the embodiment.

The radiation irradiation device 2 includes a base section 3, a gantry 4 provided on the base section 3 to be rotatably operated around a center of rotation, and an irradiation section 5 provided at the gantry 4. In addition, the CT device 6 is attached to the gantry 4.

The gantry 4 is configured to be rotatable relative to the base section 3 and is set such that an isocenter in the irradiation section 5 is in the vicinity of the center of rotation of the gantry 4.

Next, the couch 10 of the embodiment will be described.

The couch 10 includes a lifting device 11 fixed to a floor to which the radiation treatment system 1 is installed, a slide device 12 and a tilting device 21 which are attached to the lifting device 11, and a tabletop 28 connected to the tilting device 21.

The lifting device 11 is a device for moving the slide device 12, the tilting device 21, and the tabletop 28 back and forth in a direction perpendicular to the floor.

The slide device 12 is a device which is disposed on an upper end of the lifting device 11 for the purpose of moving the tilting device 21 in a horizontal direction. As shown in FIGS. 2 to 4, the slide device 12 includes a pair of first rails 13, a first moving section 14 running on the pair of first rails 13, a pair of second rails 15 provided on an upper surface of the first moving section 14, and a second moving section 16 running on the pair of second rails 15.

The pair of first rails 13 are disposed at two positions spaced apart from each other on an upper end surface of the lifting device 11. Respective rails configuring the pair of first rails 13 extend in parallel with each other. A first rack (not shown), which engages with a first pinion gear (not shown) provided on the first moving section 14, is disposed between the respective rails configuring the pair of first rails 13.

The first moving section 14 runs on the first rails 13 by a rack and pinion mechanism.

The pair of second rails 15 are arranged in one direction perpendicular to the pair of first rails 13. As shown in FIG. 4, respective rails configuring the pair of second rails 15 extend in parallel with each other. A second rack 18, which engages with a second pinion gear 19, to be described later, provided on the second moving section 16, is disposed between the respective rails configuring the pair of second rails 15.

As shown in FIGS. 3 and 4, the second moving section 16 has a pair of second sliders 17 which are slidably attached to each rail configuring the pair of second rails 15. The second sliders 17 are disposed at two positions for each rail configuring the pair of second rails 15. That is, in the embodiment, a total of four sliders 17 are attached to the pair of second rails 15. Furthermore, the second moving section 16 is provided with a second motor section 20 to which the second pinion gear 19 engaging with the second rack 18 is attached. The second motor section 20 rotatably drives the second pinion gear 19 by a control unit which is not shown. The second moving section 16 runs on the second rails 15 by rotation driving of the second pinion gear 19.

The tilting device 21 includes a pair of block bodies 22 which are movable on the respective rails configuring the pair of second rails 15, drive mechanisms 23 which linearly move the respective block bodies 22 with respect to the second moving section 16, a support section 26 supporting the tabletop 28, and levers 27 connected to the tabletop 28 and the respective block bodies 22.

Each of the block bodies 22 is a member which is movable in a direction in which the second rail 15 extends by running on the second rail 15. Movement of the block body 22 in a direction intersecting with the direction in which the second rail 15 extends is restricted. One block body 22 is provided for each rail configuring the pair of second rails 15. The two block bodies 22 run on the second rails 15 independently of each other by the drive mechanisms 23.

The drive mechanisms 23 include a first drive mechanism 23A which moves one of the pair of block bodies 22 (a block body 22A) with respect to the second moving section 16, and a second drive mechanism 23B which moves the other of the pair of block bodies 22 (a block body 22B) with respect to the second moving section 16.

The first drive mechanism 23A includes a rod-shaped threaded section 24A extending in parallel with the second rail 15 and having a thread formed on an outer surface, and a nut section 25A provided at the block body 22A so that the threaded section 24A is screwed to the nut section 25A. The threaded section 24A axially rotates relative to the nut section 25A, thereby allowing the block body 22A to move with respect to the moving section.

The second drive mechanism 23B includes a rod-shaped threaded section 24B extending in parallel with the second rail 15 and having a thread formed on an outer surface, and a nut section 25B provided at the block body 22B so that the threaded section 24B is screwed to the nut section 25B. The threaded section 24B axially rotates relative to the nut section 25B, thereby allowing the block body 22B to move with respect to the moving section.

The support section 26 is provided on the second moving section 16 and supports the tabletop 28 such that the tabletop 28 is swingable with respect to the second moving section 16. In the embodiment, the support section 26 is connected by a ball joint and the tabletop 28 rotatably moves around a center of rotation of the ball joint with respect to the second moving section 16.

As shown in FIG. 3, the levers 27 include a first lever 27A provided at one of the pair of block bodies 22 (a block body 22A), and a second lever 27B provided at the other of the pair of block bodies 22 (a block body 22B). Since the first lever 27A and the second lever 27B have a common configuration, only the configuration of the first lever 27A will be described in connection with portions of the common configuration.

One end of the first lever 27A is connected to the tabletop 28 while the other end is connected to the block body 22A. The first lever 27A is a rod-shaped member both ends of which are provided with joints having two or more degrees of freedom. For example, both of the ends of the first lever 27A are provided with universal joints or ball joints. Therefore, the first lever 27A is swingably connected to the block body 22A and the tabletop 28. The first lever 27A has an axial length longer than a distance between the second rail 15 and a lower surface of the tabletop 28 when the tabletop 28 is in a horizontal state.

One end of the second lever 27B is connected to the tabletop 28 while the other end is connected to the block body 22B. The second lever 27B is the same as the first lever 27A in terms of structures at both ends of the second lever 27B and a length of the second lever 27B.

One end of the first lever 27A (an end of a side connected to the tabletop 28) and one end of the second lever 27B (an end of a side connected to the tabletop 28) are connected to the tabletop 28 at positions different each other, wherein the positions are different from the support section 26 at the tabletop 28.

The tabletop 28 has a substantially flat plate shape. The tabletop 28 is supported at three different points by the support section 26, the first lever 27, and the second lever 27. The upper surface of the tabletop 28 constitutes a bed on which a patient (a test object) is placed.

Figure 5:
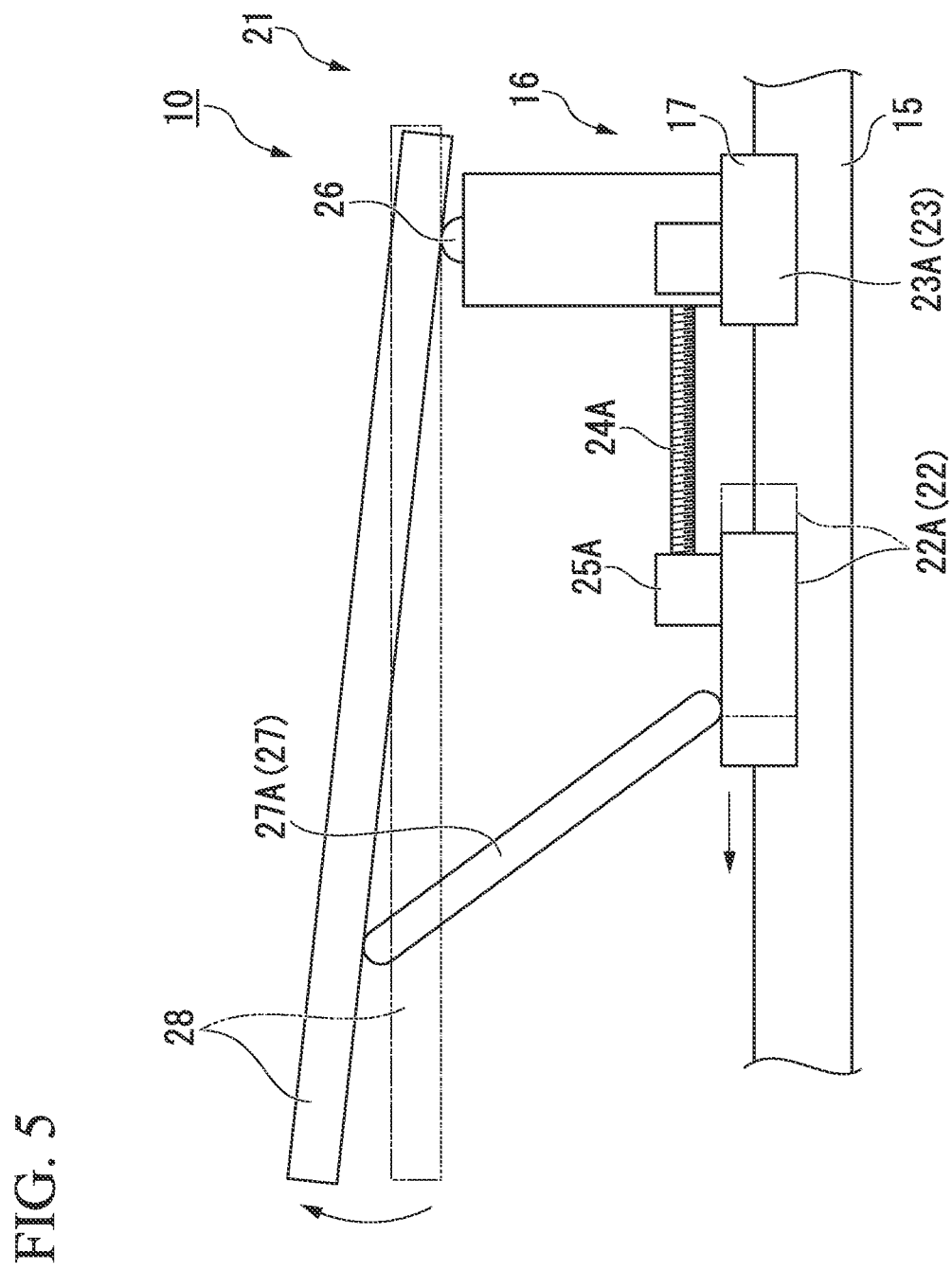
FIG. 5 is a view for describing an operation when the couch is used.
Figure 6:
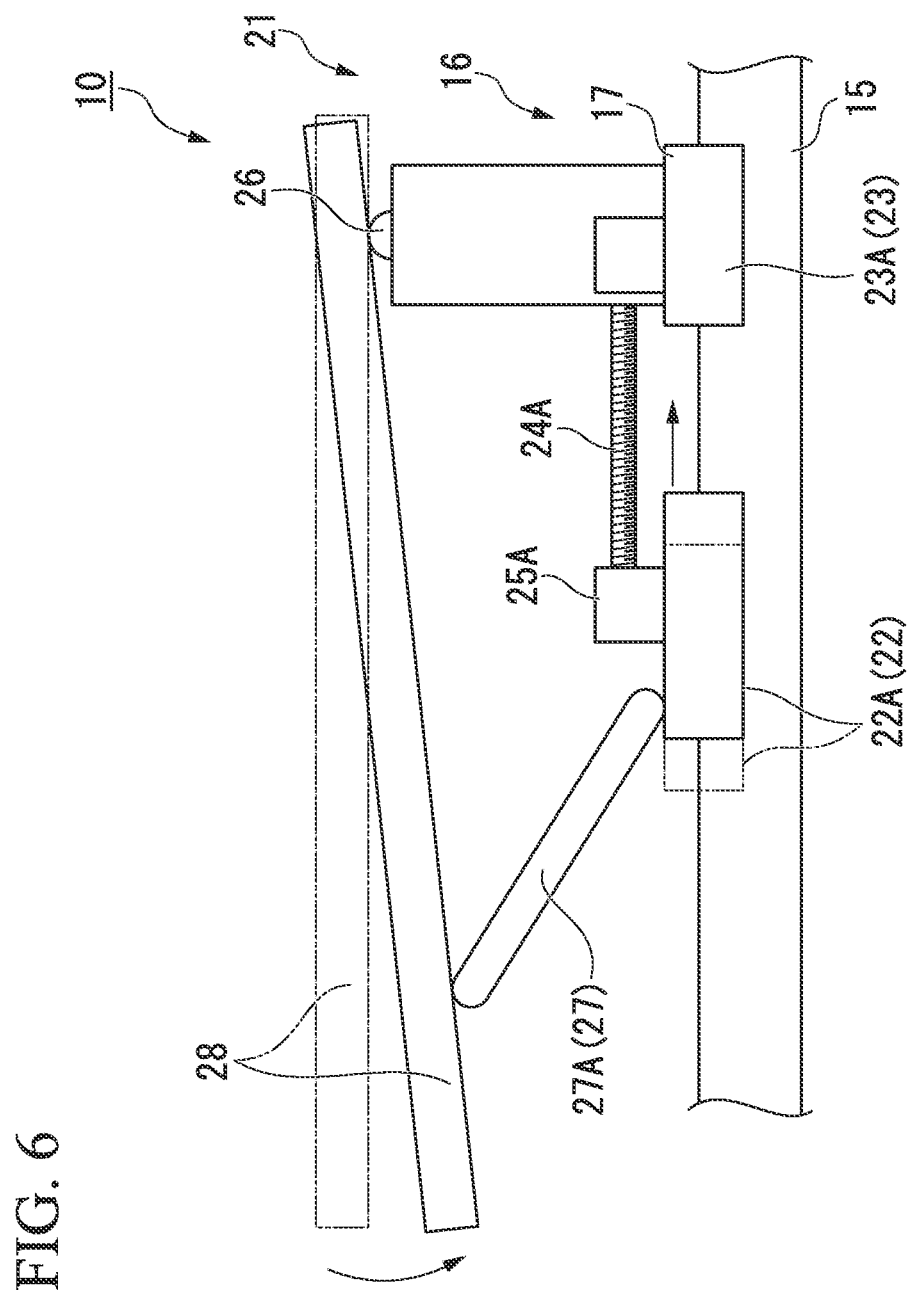
FIG. 6 is a view for describing an operation when the couch is used.

Next, an operation of the couch 10 of the embodiment will be described. FIGS. 5 and 6 are views for describing an operation when the couch 10 is used.

When the couch 10 is used, a patient is placed on the bed provided at the tabletop 28. The patient is maintained at a proper posture for being irradiated with radiation, and is maintained as necessary at a proper posture by a retainer or the like which is not shown.

Subsequently, the couch 10 is driven such that a planned position for irradiating the patient with radiation coincides with an isocenter using the lifting device 11, the slide device 12, and the tilting device 21.

The lifting device 11 shown in FIG. 1 is used for the purpose of adjusting a position of the tabletop in a direction perpendicular to the radiation treatment device. The slide device 12 is used to adjust an insertion depth of the patient into the gantry 4 or is used for the purpose of adjusting a position of the tabletop 28 in a horizontal direction thereof within the gantry 4. The tilting device 21 is used for the purpose of adjusting an inclined angle of the tabletop to the horizontal direction.

As shown in FIGS. 5 and 6, the tilting device 21 horizontally maintains the tabletop 28 in an initial state. When the tabletop 28 is tilted from the horizontal direction within the gantry 4 shown in FIG. 1, any one of the first drive mechanism 23A and the second drive mechanism 23B is driven or both are driven.

As shown in FIGS. 5 and 6, for example, by axially rotating the threaded section 24A, a distance of the block body 22A relative to the second moving section 16 in the direction in which the second rail 15 extends is changed. Here, when the second moving section 16 stops on the second rail 15, the block body 22A moves on the second rail 15 with respect to the second moving section 16. Since the block body 22A is connected to the tabletop 28 by the first lever 27A, an inclination of the first lever 27A is changed according to a movement direction and amount of movement of the block body 22 along the second rail 15.

For example, as shown in FIG. 5, when the block body 22A moves so as to approach a connection portion between one end of the first lever 27A and the tabletop 28, an inclined angle of the first lever 27A becomes larger and, as such, the tabletop 28 is pushed up by the first lever 27A. On the other hand, as shown in FIG. 6, when the block body 22A moves so as to be away from the connection portion between one end of the first lever 27A and the tabletop 28, the inclined angle of the first lever 27A becomes smaller and, as such, the tabletop 28 is lowered by the first lever 27A.

Although not shown in the drawings, by axially rotating the threaded section 24B by the same operation, a distance of the block body 22B relative to the second moving section 16 is changed so that the tabletop 28 is pushed up or lowered.

In the embodiment, since one end of the first lever 27A and one end of the second lever 27B mutually move on the basis of the support section 26 as a support point, the tabletop 28 is tilted around the support section 26 in a desired direction. For example, the tabletop 28 may pivot around an axial line parallel to the second rail 15 with respect to the second moving section 16 or the tabletop 28 may pivot around an axial line perpendicular to the second rail 15 with respect to the second moving section 16.

As such, by operating the lifting device 11, the slide device 12, and the tilting device 21, the patient may be arranged within the gantry 4 at a proper position and angle. Thereafter, by radiating radiation from the irradiation section 5, the radiation is radiated toward the isocenter so as to irradiate a position of the patient at which irradiation with radiation is planned.

Thus, according to the couch 10 of the embodiment, the block bodies 22 run on the pair of second rails 15 disposed below the tabletop 28, thereby allowing the inclined angles of the levers 27 to be changed. Therefore, the tilting device 21 may be accommodated within a space between the second rails 15 and the tabletop 28.

Thereby, the couch 10 may be minimized.

In addition, since the second sliders 17 and the block bodies 22 share the second rails 15, the number of parts may be reduced compared to a case in which rails are provided in connection with the respective second sliders 17 and block bodies 22.

Although an embodiment of the present invention has been described above with reference to the drawings, specific configurations are not limited thereto and a design modification may be made appropriately without departing from the scope of the invention.

For example, although the above-mentioned embodiment has been described as a case placing a patient, an object placed on the tabletop of the couch is not limited to a human being. For example, the object placed on the tabletop of the couch may also be an animal or an inanimate object other than a human being.

In addition, both of the ends of each of the first and second levers may also include a configuration absorbing torsion using rubber bushes, instead of provision of the joints having two or more degrees of freedom. In addition, the joint having two or more degrees of freedom may also be provided only at any one of the ends of the first and second levers.

Moreover, the first and second levers may also be configured to operate in an extendable and contractible manner.

Furthermore, a design modification of the above-mentioned embodiment is not limited to the above matters.

INDUSTRIAL APPLICABILITY

The above couch with a patient-inclining device may be applied to a couch requiring strict positioning such as a case in which a target part of a patient (a test object) is irradiated with radiation.

REFERENCE SIGNS LIST 1 radiation treatment system
2 radiation irradiation device
3 base section
4 gantries
5 irradiation section
6 CT device
10 couch
11 lifting device
12 slide device
13 first rail
14 first moving section
15 second rail 16 second moving section
17 second slider
18 second rack
19 second pinion gear
20 second motor section
21 tilting device
22 block body
23 drive mechanism
24A threaded section
24B threaded section
25A nut section
25B nut section
26 support section
27 lever
27A first lever
27B second lever
28 tabletop

The invention claimed is:

1. A couch with a patient-inclining device, comprising:
a tabletop on which a test object is placed;
a pair of rails arranged in one direction below the tabletop;
a moving section having a pair of sliders movable on the pair of rails;
a pair of block bodies movable on the pair of rails;
drive mechanisms linearly moving the block bodies in the one direction with respect to the moving section;
a support section directly connected to the moving section to support the tabletop; and
levers, each having one end connected to the tabletop and the other end connected to the associated one of the pair of block bodies, wherein the drive mechanisms comprise:
a first drive mechanism moving one of the pair of block bodies with respect to the moving section; and
a second drive mechanism moving the other of the pair of block bodies with respect to the moving section, wherein the levers comprise:
a first lever directly connected to the one of the pair of block bodies; and
a second lever directly connected to the other of the pair of block bodies, and
wherein the one end of the first lever and the one end of the second lever are connected to the tabletop at positions different from each other, wherein the positions are different from a position at which the support section supports the tabletop.

2. The couch according to claim 1, wherein at least one of the first and second drive mechanisms comprises:
a rod-shaped threaded section extending in parallel with one of the rails and having a thread formed on an outer surface; and
a nut section provided at one of the block bodies so that the threaded section is screwed to the nut section, and
wherein the threaded section axially rotates relative to the nut section, thereby allowing the block body to move with respect to the moving section.

3. The couch according to claim 1, wherein the support section connects the moving section to the tabletop such that the tabletop is pivotable around a predetermined center of rotation with respect to the moving section.

4. The couch according to claim 1, wherein at least one of the one end and the other end of each of the levers is provided with a joint having a degree of freedom of two or more axes.

* * * * *